(12) United States Patent  (10) Patent No.:  US 9,186,550 B2
Golsby et al.  (45) Date of Patent:  Nov. 17, 2015

(54) EXERCISE APPARATUS WITH A MAGNETIC RESISTANCE

(71) Applicant: Coventry University, West Midlands (GB)

(72) Inventors: Nicholas Golsby, Northamptonshire (GB); Georgios Chrysakis, West Midlands (GB); Shaun Day, Staffordshire (GB); Jonathan Beal, Worcestershire (GB); Jonathan Doel, Greater London (GB)

(73) Assignee: Coventry University, West Midlands (GB)

( * ) Notice: Subject to any disclaimer, the term of this patent is extended or adjusted under 35 U.S.C. 154(b) by 0 days.

(21) Appl. No.: 14/415,339

(22) PCT Filed: Jul. 17, 2013

(86) PCT No.: PCT/GB2013/051908
§ 371 (c)(1),
(2) Date: Jan. 16, 2015

(87) PCT Pub. No.: WO2014/013248
PCT Pub. Date: Jan. 23, 2014

(65) Prior Publication Data
US 2015/0190678 A1   Jul. 9, 2015

(30) Foreign Application Priority Data

Jul. 17, 2012  (GB) .................................. 1212663.7

(51) Int. Cl.
*A63B 71/00*  (2006.01)
*A63B 24/00*  (2006.01)
(Continued)

(52) U.S. Cl.
CPC ........... *A63B 24/0087* (2013.01); *A61B 5/1126* (2013.01); *A61B 5/222* (2013.01);
(Continued)

(58) Field of Classification Search
CPC ............. A63B 24/0087; A63B 21/002; A63B 21/0023; A63B 21/005; A63B 21/0052; A63B 21/062; A63B 21/078; A63B 21/1488; A63B 24/0062; A63B 24/0075
See application file for complete search history.

(56) References Cited

U.S. PATENT DOCUMENTS

2005/0176560 A1  8/2005  Chen
2011/0275481 A1  11/2011 Greenhill et al.

FOREIGN PATENT DOCUMENTS

DE   19517090 A1 * 11/1996
EP   1 166 826     1/2002
(Continued)

OTHER PUBLICATIONS

International Searching Authority, International Search Report and Written Opinion for PCT/GB2013/051908 mailed Nov. 29, 2013, 8 pages.

*Primary Examiner* — Glenn Richman
(74) *Attorney, Agent, or Firm* — McDonnell Boehnen Hulbert & Berghoff LLP.

(57) ABSTRACT

Exercise apparatus (1) in which a person exercising exerts a force against a movable actuator (6) to which is applied an adjustable force by a load system which resists or assists the movement of the actuator and is connected to the actuator by cables (9). The load system comprises a fixed, longitudinally arranged coaxial series of coil units (15), each coil unit being independently connectible to a source of electric current. The series of coils provides an elongate passage (18), and a shuttle (19) of ferromagnetic material is mounted for relative longitudinal movement within the passage, in response to movement of the actuator. Passage of a current through a coil unit exerts a force on the shuttle when in that coil unit, and is controlled by a microprocessor (22).

23 Claims, 6 Drawing Sheets

(51) Int. Cl.
  *A63B 21/002* (2006.01)
  *A63B 21/005* (2006.01)
  *A63B 21/062* (2006.01)
  *A63B 21/078* (2006.01)
  *A63B 21/00* (2006.01)
  *A61B 5/11* (2006.01)
  *A61B 5/22* (2006.01)
  *A63B 22/00* (2006.01)

(52) U.S. Cl.
  CPC ............ *A63B 21/002* (2013.01); *A63B 21/005* (2013.01); *A63B 21/00181* (2013.01); *A63B 21/062* (2013.01); *A63B 21/078* (2013.01); *A63B 21/1488* (2013.01); *A63B 24/0062* (2013.01); *A63B 24/0075* (2013.01); *A63B 21/0023* (2013.01); *A63B 21/0052* (2013.01); *A63B 2021/0026* (2013.01); *A63B 2022/0094* (2013.01); *A63B 2024/009* (2013.01); *A63B 2024/0068* (2013.01); *A63B 2024/0093* (2013.01); *A63B 2071/0063* (2013.01); *A63B 2071/0072* (2013.01); *A63B 2071/0081* (2013.01); *A63B 2209/08* (2013.01); *A63B 2220/13* (2013.01); *A63B 2220/20* (2013.01); *A63B 2220/30* (2013.01); *A63B 2220/40* (2013.01); *A63B 2220/51* (2013.01); *A63B 2220/72* (2013.01); *A63B 2230/06* (2013.01); *A63B 2230/42* (2013.01); *A63B 2230/50* (2013.01)

(56) References Cited

FOREIGN PATENT DOCUMENTS

| | | | | |
|---|---|---|---|---|
| GB | 002477972 B | * | 8/2011 | ......... A63B 21/0051 |
| WO | 2010/044048 | | 4/2010 | |

* cited by examiner

EXERCISE APPARATUS WITH A MAGNETIC RESISTANCE

This invention relates to exercise apparatus of the type in which a person exercising exerts a force against a movable actuator to which is applied an adjustable force by a load system which resists or assists the movement of the actuator.

It is known for the load system to utilise the magnetic force between two components. Such systems are shown in WO 2010/044048, US 2005/176560, US 2011/0275481 DE 3920727. GB 2477972 discloses an arrangement in which the load system comprises a fixed elongate stator formed of permanent magnets, around which is positioned a movable armature in the form of a coil assembly connected to a source of electrical current. The coil assembly is connected to the actuator and moves longitudinally along the stator. The level of current fed to the coil assembly determines the degree of counter-force applied by the load system.

Viewed from one aspect the present invention provides exercise apparatus comprising a movable actuator against which a force can be exerted by a user to cause movement of the actuator, and a load system which provides an adjustable force to resist or assist the force exerted by the user by means of magnetic interaction between a fixed component and a movable component which is connected to the actuator so as to move in response to movement of the actuator, one of the fixed and movable components comprising a coil assembly which is energised by electricity from a source of electric current under the control of a microprocessor control unit so as to create a magnetic field which exerts a force on the other component; characterised in that the fixed component comprises the coil assembly, which includes a longitudinally arranged coaxial series of coil units; an elongate passage is defined within the series of coil units; and the movable component comprises a shuttle of ferromagnetic or ferrimagnetic material which is not a permanent magnet, the shuttle being mounted for longitudinal movement within the passage; and wherein the supply of electric current from the source to each coil unit is independently controllable by the control unit.

In such an arrangement, when current is supplied to a coil unit in which the shuttle is located, the coil acts as an electromagnet and a magnetic field is generated which will resist movement of the shuttle if it is within the coil unit. If the shuttle is outside a coil unit, it will be attracted in to the centre of a coil unit. The shuttle will be moved along the passage by the efforts of the user, and as it passes longitudinally along the passage the source of electric current is connected to and disconnected from the coil units sequentially in the longitudinal direction, so as to maintain a chosen resistance to movement of the shuttle and thus a chosen degree of counter-force applied by the load system. The coil units can also be activated sequentially to provide assistance to the user in the direction of movement. The resistance to movement of the shuttle can be varied by altering the current through the coil units. When current is supplied to a coil unit, a magnetic field is generated which attracts the shuttle to the centre of a coil unit. The shuttle will resist movement from within the coil unit. By activating the coil units sequentially as the shuttle moves longitudinally, current is only required to pass through those coil units through which the shuttle is passing at any given time.

Because the shuttle is not a permanent magnet, the polarity of the electromagnet when a coil is activated, which depends on the direction of current through the coil, does not affect whether the shuttle is attracted to within a coil or held within a coil. If the shuttle was a permanent magnet, the polarity of the magnetic field generated would determine whether the shuttle was attracted in to a coil or repelled from it. This means that the control logic operated by the microprocessor for supplying electricity to the coil units would also have to control the direction of current through the coil units, thus making the arrangement more complex.

In some embodiments of the invention, to improve performance there may be a plurality of shuttles.

The current through a coil unit may vary as the shuttle passes through it. For example, as the shuttle move into a coil unit the current may be at a relatively high level, for example to compensate for the reduction in force on the shuttle as it passes through a reduction in the magnetic field if there is a space between a first coil unit and an adjacent second coil unit, but as the shuttle moves to a position where it is contained within the second coil unit the current may be reduced. As the shuttle leaves a first coil unit there may be an increase in the current supplied to the first coil unit until the shuttle has entered the next coil unit. When the shuttle has fully entered the next coil unit, the current to the first coil unit can be terminated.

It will be appreciated that unlike a coil gun, where passing a current through a succession of coil units projects a ferromagnetic projectile in a longitudinal direction, in the present invention each coil unit is arranged to resist or assist movement of the shuttle in the direction of intended movement under the actions of the person using the exercise machine. The exercise machine of the present invention is not arranged to shoot a projectile at high speed but is arranged to provide resistance to relatively low speed movements.

The exercise apparatus may be such that after the actuator has been moved by a user to perform an exercise, there is a restoring force to return the actuator to its original position. This restoring force could be provided by gravity in the case of apparatus that requires a user to pull up or push up or weight, or for example by a spring. In some embodiments the load system acts to damp the action of this restoring force, so as to prevent the actuator returning too quickly. In apparatus according to the invention, the coil unit will resist longitudinal movement of the shuttle out of the coil unit in either direction, and thus the load system can be used to supply a restraining force whether a user is trying to move a load in one direction or allowing it to return to the other direction. In some embodiments of apparatus in accordance with the invention, the user may have to urge an actuator in both the forwards and the return direction, and the load system can be used to supply a restraining force when a user is trying to move the actuator in either direction.

Sequential operation of the coil units and alteration of the current provided to an individual coil unit may be controlled by the microprocessor control unit so as to provide a profile as the shuttle moves through the coil units, such as a force/range of movement profile or a force/velocity profile. There may be an initial stage of mapping the system so that the desired effects can be obtained. A microprocessor control unit can be used to set up profiles of resistance to match the profile of exercise activities required for a person training for a particular sport, or to match the requirements of a person seeking to deal with a point of weakness during exercising, for example.

The system may be provided with sensors which provide information to the control unit, such as position, speed, acceleration, direction of movement and so forth. Others parameters can be detected by suitable sensors such as the ambient temperature, or parameters associated with the person exercising such as pulse rate, respiration rate, or body temperature. These are used in determination of how to control the coil units. In addition, they may activate an emergency mechanism. For example, the control unit may act if it detects that a person has reached their limit, and may reduce the load in a controlled manner. The load system may act as a damper to control lowering of a load, for example to prevent a sudden drop.

In some embodiments, sensors can measure the force and the displacement at any time. From the displacement, as a function of time, the velocity, acceleration, and rate of acceleration can be determined. The direction of displacement can also be identified.

The coil assembly, including the shuttle inside, may be encased in a casing so as to protect the assembly, which could for example be of a metal or of plastics. A conductive metal such as aluminium could be used for the casing. A metal casing can be of a ferromagnetic material. Ferromagnetic metal would act to concentrate the magnetic flux and therefore improve performance/efficiency of the system.

Although each coil unit is operated for only a short period of time whilst the shuttle is within that coil unit, there may be a need to remove excess heat and a cooling system may be provided. This may, for example, circulate cooling air around the coil assembly.

The coil units may be separated from each other by spacers, for example of plastics material or another insulating material, or for example of a ferromagnetic material such as ferrite. The shuttle may have approximately the same longitudinal extent as a coil unit, or a coil unit plus one or two spacers.

The load system of the exercise apparatus may provide substantially all of the resistance for a user of the apparatus. However, in some embodiments the load system is used in conjunction with another arrangement for providing resistance, such as a bar on which weights are placed to provide additional loads, and the load system can be used to increase the effects of the weights on the bar, or to assist the user.

The shuttle may be connected to a flexible connecting element at one end, and to a flexible connecting element at the other end, the connecting elements (which may be different parts of a single connecting element) being coupled to the actuator. Movement of the actuator in one direction will result in a pulling force on one of the connecting elements, and movement of the actuator in the reverse direction will result in a pulling force on the other of the connecting elements. The connecting elements may be cables, belts or the like.

In a typical embodiment, the actuator is a bar which has to be moved by a person exercising, and the bar is mounted adjacent both ends for sliding movement relative to a frame. Adjacent each end of the bar a mounting block is mounted for sliding movement in a guide; one end of the mounting block is connected directly or indirectly to one of the connecting elements, and the other end of the mounting block is connected directly or indirectly to the other of the connecting elements.

In some embodiments the load system may be added to existing exercise apparatus to provide additional control of the load against which a user has to exercise.

Thus viewed from a second aspect of the invention there is provided a load system for forming part of exercise apparatus of the type in which a person exercising exerts a force against a movable actuator, the load system being adapted to provide an adjustable force which assists or resists the movement of the actuator; wherein the load system provides the adjustable force by means of magnetic interaction between a fixed component and a movable component which is adapted to be connected to the actuator so as to move in response to movement of the actuator, one of the fixed and movable components comprising a coil assembly which is energised by electricity from a source of electric current under the control of a microprocessor control unit so as to create a magnetic field which exerts a force on the other component; wherein the fixed component comprises the coil assembly, which includes a longitudinally arranged coaxial series of coil units; an elongate passage is defined within the series of coil units; and the movable component comprises a shuttle of ferromagnetic or ferrimagnetic material which is not a permanent magnet, the shuttle being mounted for longitudinal movement within the passage; and wherein the supply of electric current from the source to each coil unit is independently controllable by the control unit.

Such a load system may have any of the features as discussed earlier.

In accordance with the first and second aspects of the invention, the shuttle may be of a ferromagnetic material, such as iron or some iron alloys or oxides, or a ferrimagnetic material. When current is supplied to a coil unit to create an electromagnet, a magnetic field is generated which in turn induces a magnetic field in the shuttle, and the interaction between the two fields attracts the shuttle to the centre of a coil unit. The shuttle will resist movement from within the coil unit. However, in accordance with other aspects of the invention, the shuttle could be in the form of a permanent magnet and the control of the coil units would be modified accordingly so as to control the polarity of the magnetic field.

Thus, viewed from a third aspect, the invention provides exercise apparatus comprising a movable actuator against which a force can be exerted by a user to cause movement of the actuator, and a load system which provides an adjustable force to resist or assist the force exerted by the user by means of magnetic interaction between a fixed component and a movable component which is connected to the actuator so as to move in response to movement of the actuator, one of the fixed and movable components comprising a coil assembly which is energised by electricity from a source of electric current under the control of a microprocessor control unit so as to create a magnetic field which exerts a force on the other component, which is a permanent magnet; characterised in that the fixed component comprises the coil assembly, which includes a longitudinally arranged coaxial series of coil units; an elongate passage is defined within the series of coil units; and the movable component comprises a shuttle which is mounted for longitudinal movement within the passage; and wherein the supply of electric current from the source to each coil unit is independently controllable by the control unit.

Viewed from a fourth aspect of the invention there is provided a load system for forming part of exercise apparatus of the type in which a person exercising exerts a force against a movable actuator, the load system being adapted to provide an adjustable force which resists or assists the movement of the actuator; wherein the load system provides the adjustable force by means of magnetic interaction between a fixed component and a movable component which is connected to the actuator so as to move in response to movement of the actuator, one of the fixed and movable components comprising a coil assembly which is energised by electricity from a source of electric current under the control of a microprocessor control unit so as to create a magnetic field which exerts a force on the other component, which is a permanent magnet; characterised in that the fixed component comprises the coil assembly, which includes a longitudinally arranged coaxial series of coil units; an elongate passage is defined within the series of coil units; and the movable component comprises a shuttle which is mounted for longitudinal movement within the passage; and wherein the supply of electric current from the source to each coil unit is independently controllable by the control unit.

The supply of electric current from the source to each coil unit will be controlled by the control unit not only to control which unit is activated and the current passing through the control units, but will also be controlled as regards the direction of current and thus the magnetic polarity. The coil units can be used to urge the shuttle positively from one coil unit to another coil units, and to provide a greater degree of attraction of the shuttle than is the case with a shuttle that is not a permanent magnet.

Taking into account both possibilities for the material of the shuttle, viewed from a fifth aspect of the invention, there is provided exercise apparatus comprising a movable actuator against which a force can be exerted by a user to cause movement of the actuator, and a load system which provides an adjustable force to resist or assist the force exerted by the user by means of magnetic interaction between a fixed component and a movable component which is connected to the actuator so as to move in response to movement of the actuator, one of the fixed and movable components comprising a coil assembly which is energised by electricity from a source of electric current under the control of a microprocessor control unit so as to create a magnetic field which exerts a force on the other component; characterised in that the fixed component comprises the coil assembly, which includes a longitudinally arranged coaxial series of coil units; an elongate passage is defined within the series of coil units; and the movable component comprises a shuttle which is mounted for longitudinal movement within the passage; and wherein the supply of electric current from the source to each coil unit is independently controllable by the control unit.

Similarly, viewed from a sixth aspect of the invention there is provided a load system for forming part of exercise apparatus of the type in which a person exercising exerts a force against a movable actuator, the load system being adapted to provide an adjustable force which resists or assist the movement of the actuator; wherein the load system provides the adjustable force by means of magnetic interaction between a fixed component and a movable component which is adapted to be connected to the actuator so as to move in response to movement of the actuator, one of the fixed and movable components comprising a coil assembly which is energised by electricity from a source of electric current under the control of a microprocessor control unit so as to create a magnetic field which exerts a force on the other component; wherein the fixed component comprises the coil assembly, which includes a longitudinally arranged coaxial series of coil units; an elongate passage is defined within the series of coil units; and the movable component comprises a shuttle which is mounted for longitudinal movement within the passage; and wherein the supply of electric current from the source to each coil unit is independently controllable by the control unit.

In respect of the third to sixth aspects of the invention, the features discussed earlier in connection with the first and second aspects of the invention are applicable.

Viewed from a further aspect of the invention, there is provided exercise apparatus of the type in which a person exercising exerts a force against a movable actuator to which is applied an adjustable counter-force by a load system which resists the movement of the actuator; wherein the load system comprises a coil assembly comprising a longitudinally arranged coaxial series of coil units, each coil unit being independently connectible to a source of electric current, the coil assembly providing an elongate passage within the series of coil units, and a shuttle mounted for relative longitudinal movement within the passage, in response to movement of the actuator, passage of a current through a coil unit exerting a force on the shuttle when in that coil unit.

Viewed from another aspect of the invention there is provided a load system for forming part of exercise apparatus of the type in which a person exercising exerts a force against a movable actuator to which is applied an adjustable counter-force which resists the movement of the actuator; wherein the load system comprises a coil assembly comprising a longitudinally arranged coaxial series of coil units, each coil unit being independently connectible to a source of electric current, the coil assembly providing an elongate passage within the series of coil units, and a shuttle mounted for relative longitudinal movement within the passage, the shuttle being connected to the actuator.

As regards these two aspects of the invention, preferably, the coil assembly is fixed and the shuttle moves, being connected to the actuator. The shuttle may be of a ferromagnetic material, such as iron or some iron alloys or oxides, or a ferrimagnetic material. When current is supplied to a coil unit, a magnetic field is generated which attracts the shuttle to the centre of a coil unit. The shuttle will resist movement from within the coil unit. Alternatively, the shuttle could be in the form of a permanent magnet and the control of the coil units would be modified accordingly.

The features discussed earlier in connection with the first and second aspects of the invention are applicable to the above further aspect of the invention.

Viewed from a still further aspect of the invention, there is provided exercise apparatus comprising a longitudinally arranged coaxially aligned series of coil units each coil unit being independently connectible to a source of electric current, the coil units providing an elongate passage within the series of coil units for the longitudinal displacement of a shuttle which is to be connected to an actuating member of fitness equipment; wherein the coil units, when provided with current, produce a magnetic field which in turn produces a magnetic field in the shuttle, the resulting interaction producing a longitudinally directed force which acts on the shuttle and which is transferred to the actuating member of actuation or loading source.

The force can be created over any length of displacement by the use of multiple coaxially aligned coil units allowing for the linear displacement of the shuttle. Once the shuttle has closed the air gap with one coil unit a successive coil unit can be powered up whilst the initial coil unit is powered down, this allowing the shuttle to continue generating force. The shuttle may be of equal to a single coil unit including the spacers before and after the coil unit. The shuttle may be of ferrite material. Viewed from another aspect, the invention provides a method of monitoring the use of exercise apparatus in comprising a movable actuator against which a force can be exerted by a user to cause movement of the actuator, there being sensors which can measure a parameter related to the force being exerted by the user, and a parameter related to the displacement of the actuator, including the step of determining a parameter related to the velocity of movement of the actuator and a parameter related to the acceleration of the actuator. Preferably, the method involves a step of determining a parameter related to the rate of change of the acceleration of the actuator.

The exercise apparatus may be as described above with reference to the other aspects of the invention, or may be any other type.

An embodiment of the invention will now be described by way of example and with reference to the accompanying drawings, in which.

Figure 1:
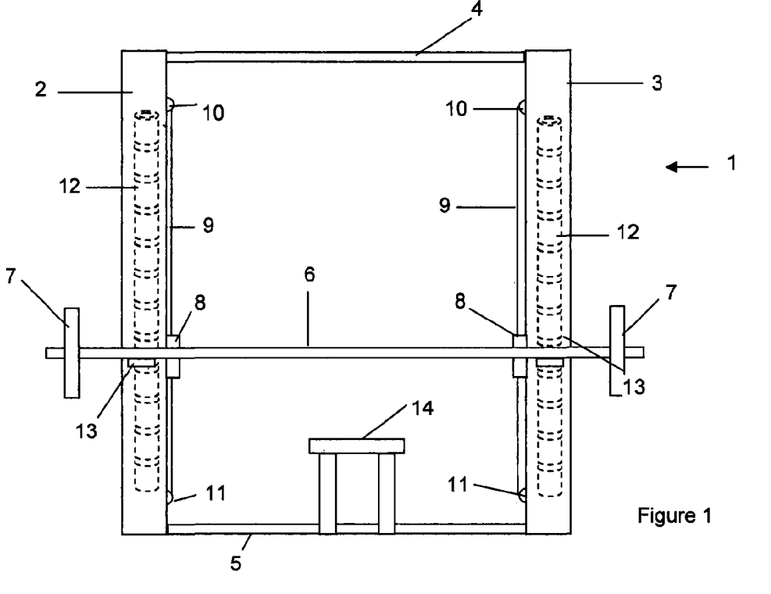
FIG. 1 is a perspective view of exercise apparatus incorporating a load system in accordance with the invention.

Referring now to FIG. 1, There is shown an exercise machine 1 comprising a frame comprising two columns 2 and 3, an upper member 4 and a lower member 5. On the frame is mounted a bar 6 carrying weights 7. The bar is attached to sliders 8 running in supports such as steel rails on the columns 2 and 3 so that the bar is guided for vertical movement, upwards under force exerted by a user and downwards under gravity. This type of machine is sometimes called a "Smith's Press". Each slider 8 is connected to a cable 9 which passes over pulleys 10 and 11 and into a coil assembly 12 mounted in each column 2 and 3. The bar 6 rests on supports 13 on the columns when not being used. A bench 14 is provided for a user.

Figure 2:
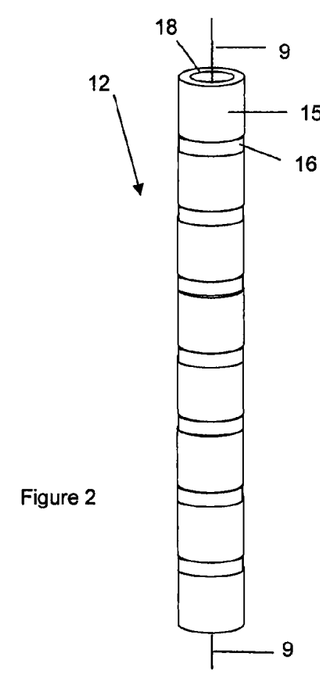
FIG. 2 is a view of a coil assembly.
Figure 3:
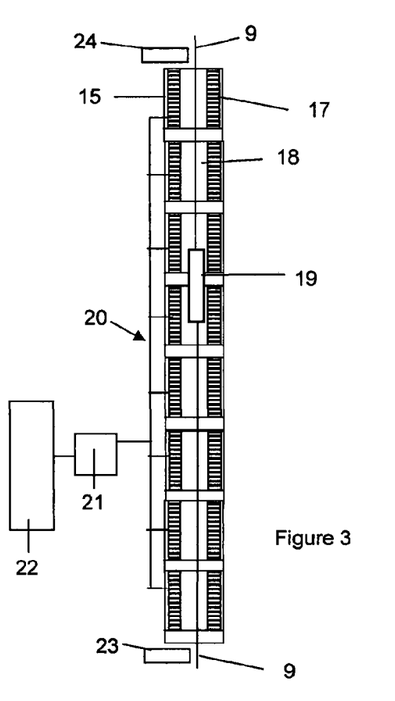
FIG. 3 is a longitudinal cross section though the coil assembly.

As shown in FIGS. 2 and 3, each coil assembly 12 comprises a vertical array of coil units 15 separated by spacers 16, which may be of ferrite material or of plastics, for example. Each coil unit includes windings 17 of conductive wire, for example copper. Passing through the array of coils is a passage 18, through which passes an upper part of cable 9 and a lower cable part of the cable 9. The cable 9 is connected to a shuttle 19 of iron, ferrite or another ferromagnetic material. The shuttle is arranged for linear movement within the coils, in accordance with movement of the bar 6.

The coil windings 17 of the individual coil units are energised selectively by means of power wires 20 supplied by a power unit controlled by a data processing system. The coil units and the shuttle provide an electromagnetic assembly to load or unload the bar 6 as desired or defined by the user or a program, in accordance with logic provided in the data processing system 22, which is supplied with data from sensors such as 23 and 24 which can detect various parameters.

Figure 4:
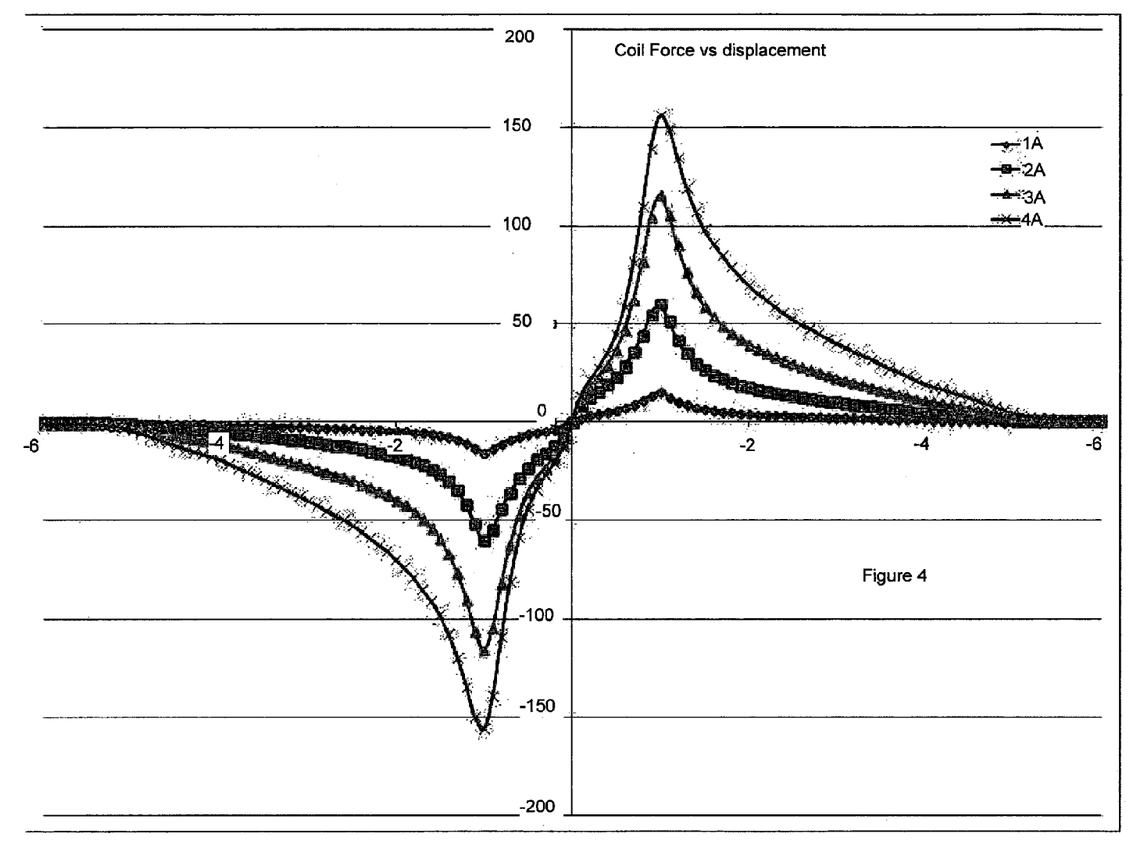
FIG. 4 shows the profile of the force generation of a coil and shuttle.

FIG. 4 shows the profile of the force generation of the electromagnet assembly. This profile shows the force produced as the shuttle displaces through the a single coil unit. This can also be described as the force produced as the air reluctance gap is closed or reduced. To the left of the y-axis the negative force generation highlights that the force can be produce positively and negatively, therefore in both directions, being loading and unloading to the user. The four curves correspond to different coil currents and different force profiles produced as the shuttle passes through a single coil unit.

Figure 5:
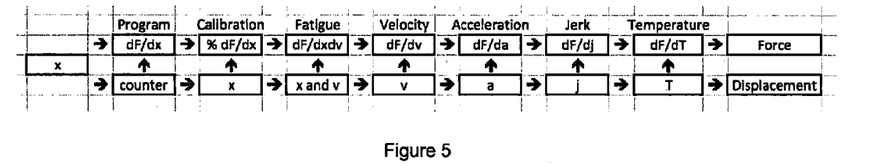
FIG. 5 is a diagram of the basic functions of the system.

FIG. 5 is an example of the basic function of the equation used to calculate the final force requested to be applied to the system. It shows the programs and requirements of the programs that make the system. Each block on the upper row can be controlled by a predefined curve that can be selected by the exercise program selection and affects the overall force requirement.

The "Program" has a repetition counter to change the corresponding curve as the system is used by the same user. It is also controls force versus position of the system.

The "Calibration" curve can be generated by the system according to the first repetition of the user. By reading the relative velocity (and therefore acceleration) of the shuttle/weights at different displacements, it can produce the strength curve of the user. The system can display this information to the user and upon selection can assist the user complete repetitions in case of injuries where the user has restricted force application over a range of motion. The system can also alter the force curve to allow more efficient and specific to the user exercise, in order to improve performance over specific range of motion. The system can be used to identify and/or map user injuries.

The "Fatigue" program monitors the user performance relative to the previous repetition and assists the user to complete repetition.

The "Velocity" program monitors the instantaneous velocity of the system and applies force according to a curve predefined by the program selected.

The "Acceleration" and "Jerk" program perform similar to the velocity but measuring acceleration. By monitoring the acceleration and jerk (rate of acceleration) the system can recognise a free fall of the weights and operate in safe mode applying maximum force controlling the descent rate of the weights.

The "Temperature" program is a safety feature that monitors the temperature of the system and reduces the system's performance if it overheats.

The system operates in open loop by measuring the position of the system over time and therefore deriving velocity, acceleration and jerk and controls the force output according to the above mentioned programs. The position of the system is controlled by the user. The system can operate in closed loop to control position, velocity or acceleration if required, in order to allow more types of exercise, by a software alteration.

FIGS. 6 to 11 demonstrate that the performance of a typical system can be altered by the addition of the invention. Due to the low electromagnetic response time of the system and fast application of force, different exercises can be simulated with this system, impulses, increasing or decreasing assistive or resistive force. These results only represent the potential behaviour of the system according to random curves used. The slope of the curves can be even more aggressive than on the figures, however, care must be taken not to injure the user.

Figure 6:
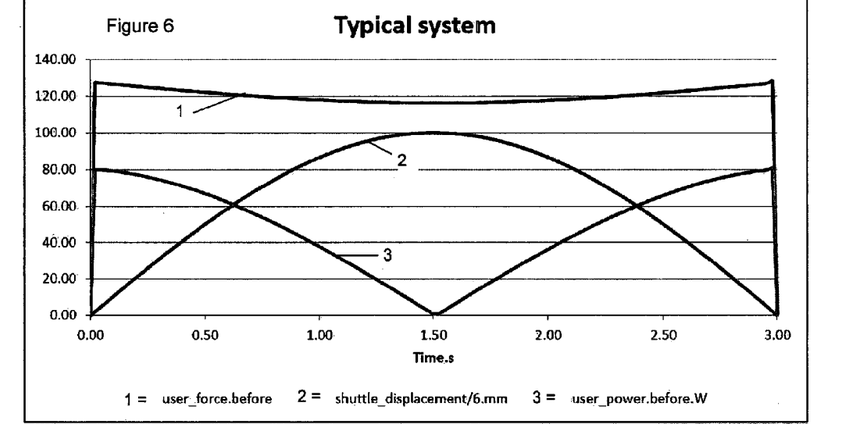
FIGS. 6-12 are diagrams showing how that the performance of a typical system can be altered by the addition of the invention.

In FIG. 6, curve 1 shows the user force required to move the weights to maximum position and back; 0-3 seconds for one repetition, as displacement (curve 2) increases to 100% and back to 0%. "Curve 3 shows the power consumption of the user.

Figure 7:
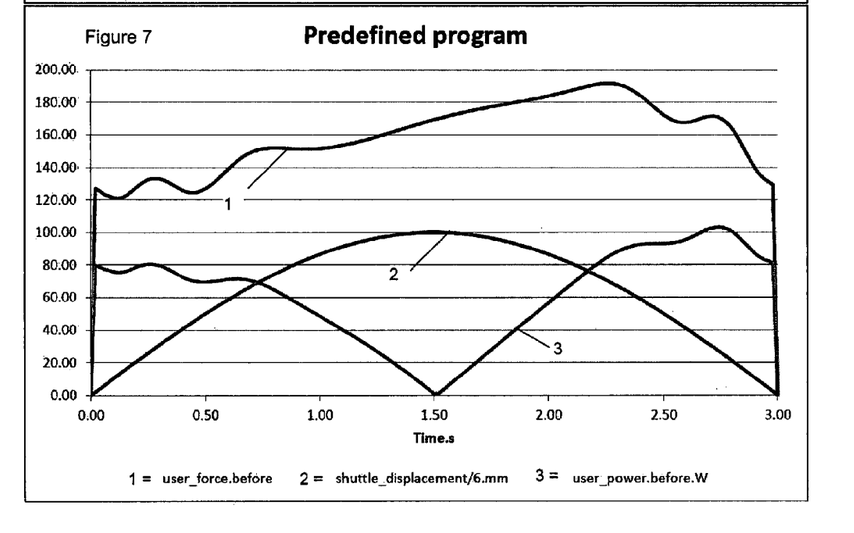

In FIG. 7, curve 1 shows the user force with the application of the system, curve 2 shows the range of motion and curve 3 shows the power consumption of the user with the application of the system.

Figure 8:
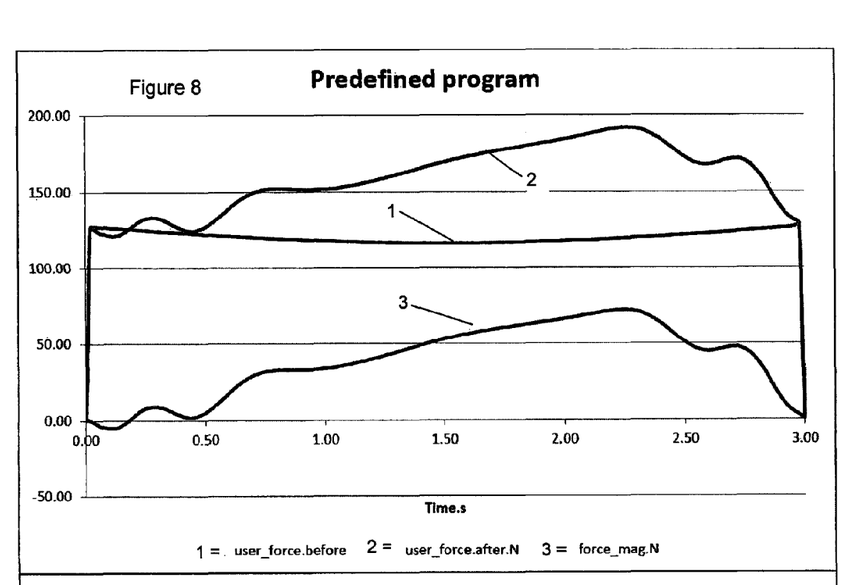

In FIG. 8, curve 1 shows the user force without the application of the system, curve 2 shows the user force with the application of the system and curve 3 shows the system force application.

Figure 9:
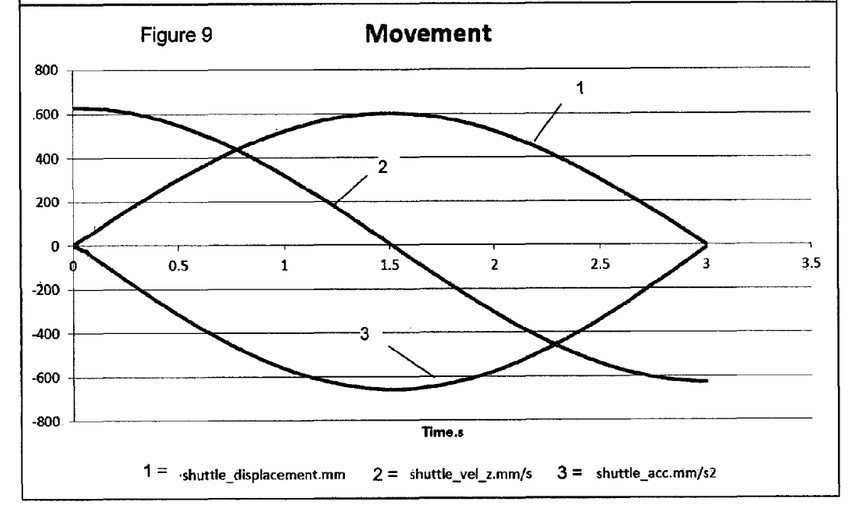

In FIG. 9, curve 1 shows the motion of the system including displacement, curve 2 the velocity and curve 3 the acceleration.

Figure 10:
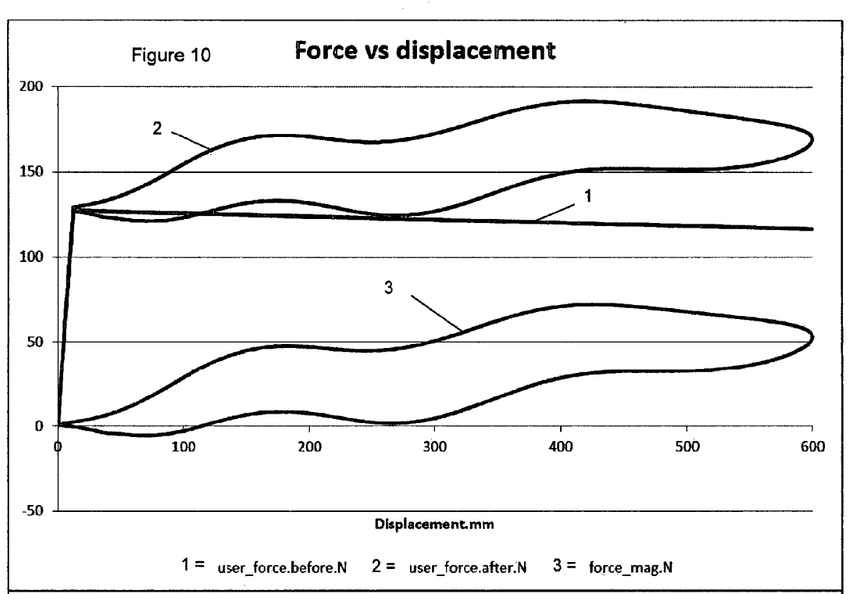

FIG. 10 is similar to FIG. 8 but relative to system displacement instead of time.

Figure 11:
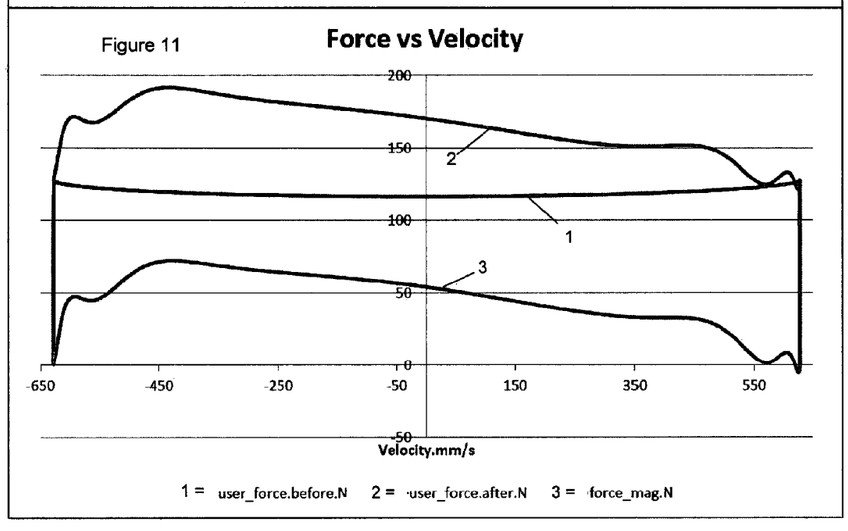

FIG. 11 is similar to FIG. 8 but relative to system velocity instead of time.

Figure 12:
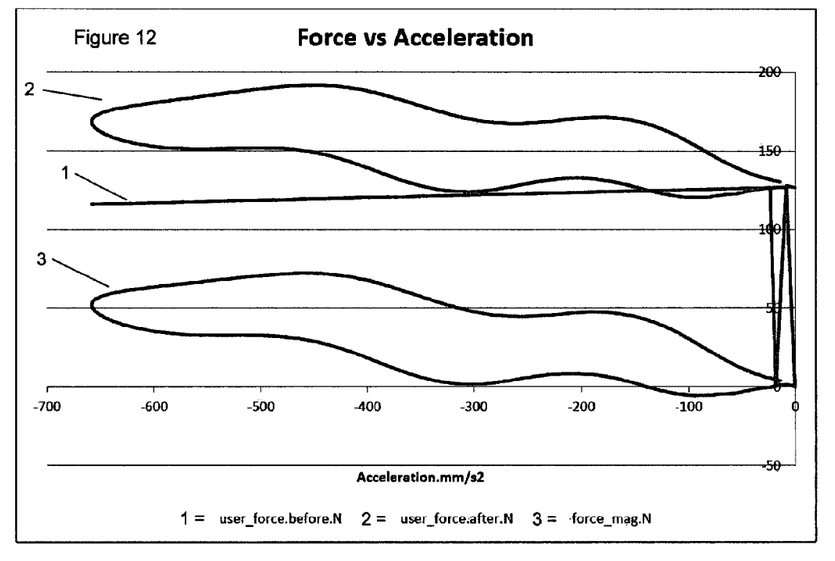

FIG. 12 is similar to FIG. 8 but relative to system acceleration instead of time.

All of the information used and recorded by this machine is derived from the relative motion between the shuttle and coil units and the user motion with respect to time and a predefined user selected programme. User motion could be collected from relative motion the interacting mechanism joints, and the connecting medium from the user motion to the loading mechanism like a weight stack. The user selected programmes can be changed with programming. This will change the initial force-displacement graph and the programming of the system accordingly. All of the variables mentioned below can be manipulated in order to produce sport specific training and rehabilitation programmes.

The outputs of the system can be tailored to the users requirements. The system can output strength curves; power curves or any other curve required that could be derived from the system variables. They can be mapped against force, power and energy in relation to time.

Each box in FIG. 5 has an associated graph and represents a stage of the programming process. X, V, A and J stand for distance, velocity, acceleration and Jerk (relative acceleration: quick/sudden movement), respectively. They are calculated from the original displacement signal, which is differentiated with respect to time.

$$v = \frac{\partial x}{\partial t}, a = \frac{\partial^2 x}{\partial t^2}, j = \frac{\partial^3 x}{\partial t^3}$$

The original displacement will be calculated with appropriate sensing apparatus such as either the use of a potentiometer or a hall-effect sensor. Two measurements will be required, one to map the displacement of the shuttle and the other to map the displacement of the handle. The system works in a coupled loop. The shuttle displacement and the handle displacement will have opposing positivity. Each value is used to calculate the force required in relation to position, direction, speed, acceleration and rate of acceleration. This information is fed to the second part of the controller, which determines the percentage of power to be sent to the coils and when to activate each coil.

The motion of the shuttle is determined as a function of the velocity. Velocity is a vector carrying speed and direction. A tan h( ) function is used to set the output of the signal to plus or minus one. This will determine the direction of motion. A change in the positivity of the velocity will indicate that a rep has been completed. This will feed back to the counter to record the number of repetitions. It will also feed to the other programs to determine the direction of motion changing the curve profile.

direction=tan$h$(1000×velocity)

The user selects a programme, which will relate force to displacement, or to a specific exercise. These programmes are predefined but can optionally be tailored and reprogrammed for different applications in order to achieve the desired output. For example, this may be an increasing load for hypertrophy training or force assistance for rehabilitation work.

The controller initially may require a calibration rep that will adjust the predefined programme and can for example include, but is not limited, to the user's range of motion, velocity, acceleration and jerk. The calibration rep records among others distance traveled over time, generating the aforementioned graphs. These graphs can feed to the exercise program to calibrate the additional force experienced by the user. In addition the user performance can be also monitored due to each repetition, and by the deviation from the calibration performance the system can estimate user fatigue and assist/resist appropriately.

Each pre-programmed variable is factored by a gain factor and by the respective force-variable graph. These graphs are summated to create a force output signal. The result is regulated by a system power adjustment factor, temperature safety factor map, free-fall control safety program or any other override safety systems. An example equation is listed below on how to calculate the force required by the system:

$$\begin{aligned}\text{force\_mag} = &(((\text{shuttle\_x\_gain} * \text{F\_x\_graph\_interpolation}) + + \\ &(\text{shuttle\_v\_gain} * \text{F\_v\_graph\_interpolation}) - - \\ &(\text{shuttle\_a\_gain} * \text{F\_a\_graph\_interpolation})) * \text{power\_adjs} + \\ &\text{safety\_overide}) ** \text{temperature\_safety}\end{aligned}$$

The shuttle position can also be replaced with host/weight stack position if there is compliance in the system.

The force_mag is the signal passed on to the coils power program in order to produce the force. This is used to calculate the users force, power and energy. Equation examples are found below:

$$\begin{aligned}\text{user\_force} = &\text{force\_mag} + \\ &((\text{handle\_mass} - \text{shuttle\_mass}) ** 9.81 * \tanh(1000 * \text{shuttle\_x})) + \\ &((\text{handle\_mass} + \text{shuttle\_mass}) ** \text{shuttle\_a}) \\ \text{user\_power} = &\text{abs}(\text{user\_force}) * \text{abs}(\text{user\_v}) \\ \text{user\_energy} = &\text{user\_power} * \text{time}\end{aligned}$$

The programming can be changed in order to make the user travel at the same speed/acceleration or force throughout the motion. A velocity over displacement graph can be displayed on a screen, requesting the user to map his motion to the displayed graph. During this motion the user can compare and adjust their performance to the required level. Similarly, the programming can be changed to apply random changes in order to train for sport specific training inertia changes like tennis or golf.

Some of the proposed applications for this equipment are listed below.

Rehabilitation.
Allow users to eventually close performance gaps due to injury.
Identifying weakness.
Identifying potential injury, subsequently preventing injury (through unloading).
Identifying fatigue and energy capacity/endurance.
Auto-spotting, providing user with 'assistance' (decreasing load) when required.
Sport Specific inertia changes and other (training as a result of acceleration and deceleration variations).
Sport Specific training to match acceleration and deceleration profiles.
Measuring Power.
Mapping Strength curves.
Negative Training.
Isokinetic Training*.
Isometric Training*.
Isotonic Training*.
Strength Tests.
Improving specific range of motion performance.
Any type of training that can benefit from on demand variable resistance/assistance with short or long response time.

Active user positioning. The actuation member can be displaced to the initial starting point which suits the user (anthropometrically and optimum ROM). Defining/Limiting the range of motion by active displacement or peak loading.

*Within the force capabilities of the machine

The system is fully scalable, as both its force capacity and maximum travel can be defined according to the host equipment/exercise requirements at build stage.

Controlling the coils is the second part of the controller. The coil control needs force and shuttle displacement to output power level requirement to the coil constant current or power regulator. It also needs an override input signal.

In normal operation the system limits the force generated to the maximum predefined level the system can achieve with the minimum amount of ripple (provide near constant force to the user through the full displacement/range of motion). For improved performance the force_mag can be normalised appropriately for smoother force variability and adjustability.

Each coil control reads the shuttle current displacement and compares to the force capacity over displacement capability of the coil. The force capacity over displacement capability of each coil can be determined during design stage or calibrated at system build. When the shuttle reaches the range where the coil can provide force to the appropriate direction, the force capability is compared to the force requirement and a percentage of power level command is sent to the coil power regulator to manage the amount of power delivered to each coil (current*voltage*time).

The override signal can be used by program specific, allowing the use of the systems peak force capacity, when the ripple of the force is not important. This case could be a free fall scenario where assistive force could reduce the force that accelerates the weight stack, therefore allow an easier to manage system. The override could also be by program where a peak force with small duration could be applied representing a sport (for example: simulating hitting a ball) or allowing a user overcome an injury range.

In embodiments of the invention, The system comprises a longitudinally arranged coaxially aligned series of coil units, each coil being independently connectible to a source of electric current. The coil assembly provides an elongate passage within the series of coil units for the longitudinal displacement of a ferrite-shuttle. The ferrite-shuttle is of equal length/height of a single coil unit including the spacers before and after the coil unit. The ferrite-shuttle is attached to the member of actuation or loading source of the required fitness equipment. The coil units, when provided with current, produce a magnetic field which in turn produces a magnetic field in the ferrite-shuttle, the resulting interaction producing a force. The electro-magnetic force generated causes the ferrite-shuttle to displace throughout the elongate passage. The generated force is transferred to the member of actuation or loading source. The force can be created over any length of displacement by the use of multiple coaxially aligned coil units allowing for the linear displacement of the ferrite material. Once the ferrite material has closed the air gap with the initial coil unit the successive coil unit can be powered to whilst the initial coil unit is powered down, this allowing the ferrite material to continue generating force and displacing.

Varying force can be generated by varying the electro-magnetic field via regulation of the current.

The current can be regulated to suit any given program/profile.

The sensing of the system produces numerous outputs such as force/ROM relationships, calorie usage, peak force and torque generation.

The outputs gained from the sensing system can also be used as inputs for the control system. These allow for personal/tailored user profiles to be generated.

The system may consist of a plurality of ferrite-shuttles of which are attached to each other and the member of actuation/loading source.

Force can be continually generated between the coil units and ferrite-shuttle by sequentially activating the required coil unit relative to the location of the ferrite-shuttle.

Embodiments of the invention therefore provide fitness apparatus that comprises of; a longitudinally arranged coaxially aligned series of coil units each coil being independently connectible to a source of electric current. The coil assembly provides a elongate passage within the series of coil units for the longitudinal displacement of a shuttle. The system produces a force to provide resistance to the user during an exercise. The apparatus may comprise multiple coil units coaxially arranged, the elongate passage inside the coil units, and/or numerous shuttles, attachment between the shuttle/s to the member of actuation or loading source, a control and sensing system.

The resistance provided to the user by the force generated by the system can varied by regulation of the current to the coil units. Force can be continually generated between the coil units and shuttle by sequentially activating the required coil unit relative to the location of the shuttle. Force can be generated by between the coil units and shuttle in both directions (positive and negative) by sequential activation of the coil units. The shuttle displaces as a result of the displacement of the member actuation, causing them to both move relative to each other. The shuttle is attached so as to provide force to the user.

In another embodiment of the invention the shuttle can exceed the length/height of a coil unit allowing the shuttle to have a reduced 'air reluctance gap' to close in the successive coil unit. In another embodiment of the invention the shuttle can be replaced with a permanent magnet of which to interact with the magnetic field of the coil units. The interaction between the permanent magnetic shuttle and coil units allows a push or pull force to be generated. By varying the polarity of the magnetic field generated by the coils capability and efficiency of the system can be improved. In an embodiment of the invention utilising a permanent magnetic shuttle, the coil units can be used to generate electricity due the displacement of the permanent magnetic shuttle relative.

When the coil units are not provided with a current then no force is generated between the coil units and the shuttle; this allows the fitness apparatus to be operated as standard without the utilisation of variable force/resistance.

At least in an embodiment of the invention, there is provided exercise apparatus (1) in which a person exercising exerts a force against a movable actuator (6) to which is applied an adjustable force by a load system which resists or assists the movement of the actuator and is connected to the actuator by cables (9). The load system comprises a fixed, longitudinally arranged coaxial series of coil units (15), each coil unit being independently connectible to a source of electric current. The series of coils provides an elongate passage (18), and a shuttle (19) of ferromagnetic material is mounted for relative longitudinal movement within the passage, in response to movement of the actuator. Passage of a current through a coil unit exerts a force on the shuttle when in that coil unit, and is controlled by a microprocessor (22).

What is claimed is:

1. Exercise apparatus comprising a movable actuator against which a force can be exerted by a user to cause movement of the actuator, and a load system which provides an adjustable force to resist or assist the force exerted by the user by means of magnetic interaction between a fixed component and a movable component which is connected to the actuator so as to move in response to movement of the actuator, one of the fixed and movable components comprising a coil assembly which is energised by electricity from a source of electric current under the control of a microprocessor control unit so as to create a magnetic field which exerts a force on the other component; characterised in that the fixed component comprises the coil assembly, which includes a longitudinally arranged coaxial series of coil units; an elongate passage is defined within the series of coil units; and the movable component comprises a shuttle which is mounted for longitudinal movement within the passage; and wherein the supply of electric current from the source to each coil unit is independently controllable by the control unit, and wherein the source of electric current is connected to and disconnected from the coil units sequentially in a longitudinal direction as the shuttle moves in that longitudinal direction.

2. Apparatus as claimed in claim 1, wherein the shuttle is of ferromagnetic or ferrimagnetic material which is not a permanent magnet.

3. Apparatus as claimed in claim 2, wherein the shuttle is of ferrite.

4. Apparatus as claimed in claim 1, wherein the shuttle is connected to a first flexible connecting element at one end, and to a second flexible connecting element at the other end, the connecting elements being coupled to the actuator.

5. Apparatus as claimed in claim 1, wherein there is maintained a chosen resistance to movement of the shuttle and thus a chosen degree of counter-force applied by the load system.

6. Apparatus as claimed in claim 1, wherein the microprocessor control unit controls sequential operation of the coil units.

7. Apparatus as claimed in claim 6, wherein the resistance to movement of the shuttle is varied by altering the current through the coil units.

8. Apparatus as claimed in claim 7, wherein the microprocessor control unit controls alteration of the current provided to an individual coil unit so as to provide a profile as the shuttle moves through the coil unit.

9. Apparatus as claimed claim 8, wherein the microprocessor control unit is used to set up profiles of resistance to match the profile of exercise activities required for a person.

10. Apparatus as claimed in claim 6, wherein the system is provided with sensors which provide information to the control unit.

11. Apparatus as claimed in claim 10, wherein the control unit determines information including velocity, acceleration and direction of movement, which are used in determination of how to control the coil units.

12. Apparatus as claimed in claim 10, wherein if the control unit detects that a person has reached their limit, the control unit reduces the load in a controlled manner.

13. Apparatus as claimed in claim 10, wherein the control unit controls the load system to act as a damper to control lowering of a load.

14. Apparatus as claimed in claim 1, wherein the coil units are separated from each other by spacers.

15. Apparatus as claimed in claim 14, wherein the spacers are of plastics material or of ferrite.

16. Apparatus as claimed in claim 1, wherein the current through a coil unit varies as the shuttle passes through it.

17. Apparatus as claimed in claim 16, wherein as the shuttle move from a first coil unit into a second coil unit, the current in the second coil unit is at a relatively high level, and as the shuttle becomes contained within the second coil unit the current is reduced.

18. Apparatus as claimed in claim 17, wherein as the shuttle leaves the first coil unit there is an increase in the current supplied to the first coil unit until the shuttle has entered the second coil unit.

19. Apparatus as claimed in claim 18, wherein when the shuttle has fully entered the second coil unit, the current to the first coil unit is terminated.

20. Apparatus as claimed in claim 1 wherein the actuator is a bar which has to be moved by a person exercising, and the bar is mounted adjacent both ends for sliding movement relative to a frame.

21. Apparatus as claimed in claim 1, wherein the source of electric current is connected to and disconnected from the coil units sequentially in the longitudinal direction, so as to maintain a chosen resistance to movement of the shuttle.

22. Apparatus as claimed in claim 1, wherein the source of electric current is connected to and disconnected from the coil units sequentially in the longitudinal direction, so as to provide assistance to the user in the direction of movement.

23. Exercise apparatus comprising a movable actuator against which a force can be exerted by a user to cause movement of the actuator, and a load system which provides an adjustable force to resist or assist the force exerted by the user by means of magnetic interaction between a fixed component and a movable component which is connected to the actuator so as to move in response to movement of the actuator, the fixed components comprising a coil assembly which is energised by electricity from a source of electric current under the control of a microprocessor control unit so as to create a magnetic field which exerts a force on the other component which is movable; wherein the coil assembly includes a longitudinally arranged coaxial series of coil units; an elongate passage is defined within the series of coil units; and the movable component comprises a shuttle of ferromagnetic or ferrimagnetic material which is not a permanent magnet, the shuttle being mounted for longitudinal movement within the passage; and wherein the supply of electric current from the source to each coil unit is independently controllable by the control unit, and wherein the source of electric current is connected to and disconnected from the coil units sequentially in a longitudinal direction as the shuttle moves in that longitudinal direction.

* * * * *